United States Patent
Ganatra et al.

(10) Patent No.: US 11,040,170 B2
(45) Date of Patent: Jun. 22, 2021

(54) CONTINUOUS FORMATION OF TUBES OF POLY-4-HYDROXYBUTYRATE AND COPOLYMERS THEREOF

(71) Applicant: Tepha, Inc., Lexington, MA (US)

(72) Inventors: Amit Ganatra, Attleboro, MA (US); Said Rizk, Windham, NH (US)

(73) Assignee: TEPHA, INC., Lexington, MA (US)

( * ) Notice: Subject to any disclaimer, the term of this patent is extended or adjusted under 35 U.S.C. 154(b) by 340 days.

(21) Appl. No.: 15/983,773

(22) Filed: May 18, 2018

(65) Prior Publication Data

US 2018/0339129 A1 Nov. 29, 2018

Related U.S. Application Data

(60) Provisional application No. 62/511,069, filed on May 25, 2017.

(51) Int. Cl.
| | | |
|---|---|---|
| *A61M 25/00* | (2006.01) | |
| *A61N 5/10* | (2006.01) | |
| *C08J 5/00* | (2006.01) | |
| *A61L 29/06* | (2006.01) | |
| *A61L 29/16* | (2006.01) | |
| *A61L 29/18* | (2006.01) | |
| *A61L 29/04* | (2006.01) | |

(Continued)

(52) U.S. Cl.
CPC ......... *A61M 25/0009* (2013.01); *A61L 29/02* (2013.01); *A61L 29/043* (2013.01); *A61L 29/045* (2013.01); *A61L 29/049* (2013.01); *A61L 29/06* (2013.01); *A61L 29/148* (2013.01); *A61L 29/16* (2013.01); *A61L 29/18* (2013.01); *A61L 31/06* (2013.01); *A61L 31/148* (2013.01); *A61L 31/16* (2013.01); *A61L 31/18* (2013.01); *A61N 5/1001* (2013.01); *B29B 13/045* (2013.01); *B29B 13/065* (2013.01); *B29C 48/0018* (2019.02); *B29C 48/022* (2019.02); *B29C 48/09* (2019.02); *B29C 48/10* (2019.02); *B29C 48/802* (2019.02); *B29C 48/902* (2019.02); *B29C 48/903* (2019.02); *B29C 48/905* (2019.02); *B29C 48/919* (2019.02); *B29C 48/9115* (2019.02); *B29C 48/92* (2019.02); *B29C 55/24* (2013.01); *C08J 5/00* (2013.01); *A61L 2300/112* (2013.01); *A61L 2300/404* (2013.01); *A61L 2300/406* (2013.01); *A61L 2300/44* (2013.01); *A61L 2300/442* (2013.01); *A61M 25/0108* (2013.01); *A61M 2205/0205* (2013.01); *A61M 2207/00* (2013.01); *B29C 2948/92152* (2019.02); *B29C 2948/92447* (2019.02); *B29K 2067/00* (2013.01); *B29K 2995/006* (2013.01); *B29L 2031/7542* (2013.01); *C08J 2367/00* (2013.01)

(58) Field of Classification Search
CPC .......... C08L 67/04; A61L 29/06; A61L 31/06; A61L 2300/112; A61L 2300/404; A61L 2300/406; A61L 2300/44; A61L 2300/442; A61L 29/02; A61L 29/043; A61L 29/045; A61L 29/049; A61L 29/148; A61L 29/16; A61L 29/18; A61L 31/148; A61L 31/16; A61L 31/18; A61M 2205/0205; A61M 2207/00; A61M 25/0009; A61M 25/0108; A61N 5/1001; B29B 13/045; B29B 13/065; B29C 2948/92152; B29C 2948/92447; B29C 48/0018; B29C 48/022; B29C 48/09; B29C 48/10; B29C 48/802; B29C 48/902; B29C 48/903; B29C 48/905; B29C 48/9115; B29C 48/919; B29C 55/24; B29C 48/92; B29K 2067/00; B29K 2995/006; B29L 2031/7542; C08J 2367/00; C08J 5/00
See application file for complete search history.

(56) References Cited

U.S. PATENT DOCUMENTS

| | | |
|---|---|---|
| 3,456,044 A | 7/1969 | Pahlke |
| 5,811,272 A | 9/1998 | Snell |

(Continued)

FOREIGN PATENT DOCUMENTS

| | | |
|---|---|---|
| WO | 9932536 | 7/1999 |
| WO | 0056376 | 9/2000 |

(Continued)

OTHER PUBLICATIONS

Hori, et al., "Chemical synthesis of high molecular weight poly(3-hydroxybutyrate-co-4-hydroxybutyrate)", Polymer 36:4703-5 (1995).

(Continued)

*Primary Examiner* — Robert S Walters, Jr.
(74) *Attorney, Agent, or Firm* — Pabst Patent Group LLP

(57) ABSTRACT

Methods have been discovered that make it possible to continuously extrude tubes of P4HB and copolymers thereof. These methods allow tubes of P4HB and copolymers thereof to be produced without radial deformation of the tubes despite the slow crystallization of the polymer and copolymers. The methods can produce tubes of P4HB and copolymers thereof with tightly defined outside and inside diameters which are required for medical application. These tubes are produced by radial expansion at temperatures above the melting temperature of P4HB and copolymers thereof, and using low tube cooling temperatures and prolonged cooling times. The tubes made from P4HB and copolymers thereof are flexible, and can be prepared with high elongation to break values.

19 Claims, No Drawings

(51) Int. Cl.

| | | |
|---|---|---|
| A61L 29/02 | (2006.01) |
| B29C 48/09 | (2019.01) |
| B29C 48/00 | (2019.01) |
| B29C 48/88 | (2019.01) |
| B29B 13/06 | (2006.01) |
| B29C 48/80 | (2019.01) |
| B29C 55/24 | (2006.01) |
| A61L 31/16 | (2006.01) |
| B29C 48/92 | (2019.01) |
| B29C 48/10 | (2019.01) |
| B29C 48/90 | (2019.01) |
| A61L 31/06 | (2006.01) |
| B29B 13/04 | (2006.01) |
| A61L 29/14 | (2006.01) |
| A61L 31/14 | (2006.01) |
| A61L 31/18 | (2006.01) |
| B29K 67/00 | (2006.01) |
| B29L 31/00 | (2006.01) |
| A61M 25/01 | (2006.01) |

(56) References Cited

U.S. PATENT DOCUMENTS

| | | |
|---|---|---|
| 6,214,283 B1 | 4/2001 | Visscher |
| 6,245,537 B1 | 6/2001 | Williams |
| 6,316,262 B1 | 11/2001 | Huisman |
| 6,323,010 B1 | 11/2001 | Skraly |
| 6,548,569 B1 | 4/2003 | Williams |
| 6,555,123 B2 | 4/2003 | Williams |
| 6,585,994 B2 | 7/2003 | Williams |
| 6,610,764 B1 | 8/2003 | Martin |
| 6,623,748 B2 | 9/2003 | Clokie |
| 6,828,357 B1 | 12/2004 | Martin |
| 6,838,493 B2 | 1/2005 | Williams |
| 6,867,247 B2 | 3/2005 | Williams |
| 6,867,248 B1 | 3/2005 | Martin |
| 6,878,758 B2 | 4/2005 | Signer |
| 7,025,980 B1 | 4/2006 | Williams |
| 7,179,883 B2 | 2/2007 | Williams |
| 7,244,442 B2 | 7/2007 | Williams |
| 7,268,205 B2 | 9/2007 | Williams |
| 7,553,923 B2 | 6/2009 | Williams |
| 7,618,448 B2 | 11/2009 | Schmitz |
| 7,641,825 B2 | 1/2010 | Rizk |
| 7,943,683 B2 * | 5/2011 | Rizk ............ A61L 27/34 523/113 |
| 8,016,883 B2 | 9/2011 | Coleman |
| 8,034,270 B2 | 10/2011 | Martin |
| 8,039,237 B2 | 10/2011 | Martin |
| 8,231,889 B2 | 7/2012 | Williams |
| 8,287,909 B2 | 10/2012 | Martin |
| 8,747,468 B2 | 6/2014 | Martin |
| 9,532,867 B2 | 1/2017 | Felix |
| 9,555,155 B2 | 1/2017 | Ganatra |
| 2007/0182041 A1 | 8/2007 | Rizk |
| 2012/0271396 A1 | 10/2012 | Zheng |
| 2014/0100649 A1 | 4/2014 | Gada |
| 2015/0313700 A1 | 11/2015 | Rizk |

FOREIGN PATENT DOCUMENTS

| | | |
|---|---|---|
| WO | 04101002 | 11/2004 |
| WO | 06015276 | 2/2006 |
| WO | 2007092417 | 8/2007 |
| WO | 2008013699 | 1/2008 |
| WO | 2011119742 | 9/2011 |
| WO | 2011159784 | 12/2011 |
| WO | 2012064526 | 5/2012 |
| WO | 2014045068 | 3/2014 |

OTHER PUBLICATIONS

Houk, et al., " Why delta-valerolactone polymerizes and gamma-butyrolactone does not polymerize", J. Org. Chem., 2008, 73 (7):2674-8 (2005).

Martin, et al., "Characterization of poly-4-hydroxybutyrate mesh for hernia repair applications," J. Surg. Res., 184:766-73 (2013).

Martin, et al., "Medical Applications of Poly-4hydroxybutyrate: A Strong Flexible Absorbable Biomaterial", Biochem. Eng. J., 16:97-105 (2003).

Moore, et al., "Chemosynthesis of bioresorbable poly(gamma-butyrolactone) by ring-opening polymerisation: a review", Biomaterials 26:3771-3782 (2005).

Steinbuchel, "Diversity of bacterial polyhydroxyalkanoic acids", FEMS Microbial. Lett. 128:219-28 (1995).

Williams, et al., "Controlled hydrolysis of poly-4-hydroxybutyrate and copolymers", Polyesters, III, 4:91-127 (2002).

Williams, et al., "Poly-4-hydroxybutyrate (P4HB): a new generation of resorbable medical devices for tissue repair and regeneration", Biomed. Tech. (Berl) 58(5):439-452 (2013).

* cited by examiner

CONTINUOUS FORMATION OF TUBES OF POLY-4-HYDROXYBUTYRATE AND COPOLYMERS THEREOF

CROSS-REFERENCE TO RELATED APPLICATION

This application claims benefit of and priority to U.S. Application No. 62/511,069 filed on May 25, 2017, the disclosure of which is incorporated herein in its entirety.

FIELD OF THE INVENTION

The present invention generally relates to processes for the continuous extrusion of tubes comprising poly-4-hydroxybutyrate and copolymers thereof, the tubes formed by these methods, and the use of the tubes as implants.

BACKGROUND OF THE INVENTION

The medical industry currently uses small diameter tubes for a wide range of applications. Applications include catheters, such as urinary and vascular catheters, intravenous lines, dialysis tubing, sheaths for self-expanding stents, inflation lumens for balloons, suction lumens for atherectomy devices, and lumens for catheter-steering wires.

Small diameter tubes are also used to make stents, and in particular, resorbable tubes have been prepared and machined to form resorbable stents. An example is the Absorb™ bioresorbable cardiovascular stent made by Abbott. This stent is made from polylactic acid (PLA), however, it degrades very slowly in vivo requiring as long as 3 years to completely degrade. PLA is also a very stiff polymer with a high modulus limiting its suitability for many applications.

Methods have been disclosed to produce resorbable tubes made from PLA. US Patent Application No. 20140100649 to Gada et al. discloses a method of fabricating a low crystallinity PLLA (poly(L-lactide)) tube suitable for use in medical device applications. The method discloses the need to radially expand the PLLA tube at a temperature of 60° C. to 100° C., which is a temperature range below the polymer's melt temperature (of about 180° C.). These conditions produced PLLA tubes with increased radial strength and a crystallinity between 20% and about 50%.

Resorbable tubes made from PLLA are however limited in their medical application because of the polymer's very slow degradation rate, and also because PLLA has a very high modulus, meaning that PLLA tubes are very stiff. It would therefore be desirable to make resorbable tubes from a faster degrading and more flexible resorbable polymer. Such tubes could be used, for example, to make stents for use in peripheral and urological applications.

Poly-4-hydroxybutyrate (Tepha's P4HB™ polymer) is a resorbable biosynthetic polymer that degrades faster than PLLA, and is much more flexible than PLLA. US Patent Application No. 2007/0182041 to Rizk et al. discloses the use of P4HB to toughen PLLA in order to make tubes with improved toughness and lower stiffness. Toughening of PLLA with P4HB did decrease the Young's modulus of the PLLA from 6.86 GPa to 1.68-2.96 GPa for the blends, however, the toughened PLLA was still relatively stiff and only had elongation to break values of 16.7 to 24.3% compared to 4% for PLLA. In comparison, the elongation to break of P4HB is 1,000%, and the Young's modulus of P4HB is 70 MPa.

Thus, there remains a need to develop resorbable tubes that have improved flexibility (lower modulus), higher elongation to break, and faster degradation.

It is an object of the present invention to provide processes to make resorbable tubes from P4HB that degrade more quickly than PLA tubes, have higher elongation to break values, and are more flexible with lower tensile modulus values than PLA tubes.

It is another object to provide flexible resorbable P4HB tubes that may optionally be further processed for use in medical implants.

SUMMARY OF THE INVENTION

Methods have been discovered that make it possible to continuously extrude tubes of P4HB and copolymers thereof. These methods allow tubes of P4HB and copolymers thereof to be produced without radial deformation of the tubes despite the slow crystallization of the polymer and copolymers. Thus, the method can produce tubes of P4HB and copolymers thereof with tightly defined outside and inside diameters which are required for medical application. These tubes are produced by radial expansion at temperatures above the melting temperature of P4HB and copolymers thereof, and using low tube cooling temperatures and prolonged cooling times. In comparison to existing resorbable tubes made, for example, from poly-L-lactide, tubes made from P4HB and copolymers thereof are more flexible with a lower tensile modulus, may have higher elongation to break values, and degrade faster in vivo

DETAILED DESCRIPTION OF THE INVENTION

Methods have been developed to produce resorbable tubes for use in medical implants. The tubes are flexible with low tensile modulus values, may have high elongation to break values, and degrade in vivo faster than tubes made from PLLA. The tubes may be further processed for use as medical devices. For example, the tubes may be cut to form stents. The disclosed herein methods allow P4HB tubes to be produced without radial deformation. Radial deformation results in variations the internal and external diameters of the tube, which in turn causes problems with flow rates through the tube, for example, inconsistent flow rates. Radial deformation presents a problem if tubes so deformed were used as a stent as it might not lodge in the vessel wall correctly if the diameters were varying.

The resorbable tubes are made from P4HB or copolymer thereof. Tubes made from P4HB and copolymers thereof have very different properties from tubes made of PLLA. Therefore, methods that have been used to produce PLLA tubes, for example by Gada et al. as disclosed in US Patent Application No. 20140100649, are not adequate to create tubes made from P4HB and copolymers thereof. This is because there are a number of significant property differences between PLLA and P4HB. First, PLLA has a glass transition temperature ($T_g$) of 60-65° C. whereas P4HB has a glass transition temperature of −51° C. As a result, PLLA is a glass at room temperature while P4HB is in a rubbery state at room temperature. This necessitates different processing conditions for P4HB and PLLA. Second, PLLA crystallizes as it cools much faster than P4HB. The difference in crystallization rates makes it particularly challenging to produce P4HB tubes without any radial deformation. Third, there is a big difference in the melt temperature of PLLA and P4HB. PLLA melts at about 180° C. whereas P4HB melts at about 61° C. Gada's method in US Patent Application No. 20140100649 discloses radial expansion of PLLA tubes at a temperature below the melt temperature of PLLA. However, to prepare P4HB tubes, it is necessary to expand P4HB tubes above the melt temperature of P4HB.

The methods disclosed herein are based upon the discovery that P4HB can be continuously extruded into tubes without any radial deformation provided the tubes are radially expanded above the melt temperature of the polymer, cooled to low temperatures, and maintained at a low temperature for a prolonged period.

I. Definitions

"Bioactive agent" is used herein to refer to therapeutic, prophylactic, and/or diagnostic agents. These include physiologically or pharmacologically active substances that act locally or systemically in the body. A biologically active agent is a substance used for, for example, the treatment, prevention, diagnosis, cure, or mitigation of one or more symptoms or characteristics of a disease or disorder, a substance that affects the structure or function of the body, or pro-drugs, which become biologically active or more active after they have been placed in a predetermined physiological environment. Bioactive agents include biologically, physiologically, or pharmacologically active substances that act locally or systemically in the human or animal body. Examples can include, but are not limited to, small-molecule drugs, peptides, proteins, sugars, polysaccharides, nucleotides, oligonucleotides, and nucleic acid molecules such as aptamers, siRNA, miRNA and combinations thereof.

"Biocompatible" as generally used herein means the biological response to the material or device is appropriate for the device's intended application in vivo. Metabolites of these materials should also be biocompatible.

"Blend" as generally used herein means a physical combination of different polymers, as opposed to a copolymer comprised of two or more different monomers.

"Copolymers of poly-4-hydroxybutyrate" as generally used herein means any polymer comprising 4-hydroxybutyrate with one or more different hydroxyalkanoic acid units.

"Elongation" or "extensibility" of a material means the amount of increase in length resulting from, as an example, the tension to break a specimen. It is expressed usually as a percentage of the original length. (Rosato's Plastics Encyclopedia and Dictionary, Oxford Univ. Press, 1993).

"Load at Yield" as used herein is measured at the point the material begins to plastically deform, whereas "Load" as used herein is measured at the point the material breaks.

"Molecular weight" as used herein, unless otherwise specified, refers to the weight average molecular weight (Mw), not number average molecular weight (Mn), and is measured by gel permeation chromatography (GPC) relative to polystyrene.

"Polyhydroxyalkanoates" or "PHAs" are linear polyesters produced by bacterial fermentation. Depending upon the microorganism and the cultivation conditions, homo- or copolyesters with different hydroxyalkanoic acids are generated.

"Poly-4-hydroxybutyrate" as used herein means a homopolymer comprising 4-hydroxybutyrate units. It may be referred to herein as Tepha's P4HB™ polymer or as TephaFLEX® biomaterial (manufactured by Tepha, Inc., Lexington, Mass.). Polyhydroxybutyrate as generally used in the literature refers to the naturally occurring polymer poly-3-hydroxybutyrate.

"Resorbable" as generally used herein means the material is broken down in the body and eventually eliminated from the body. The terms "resorbable", "degradable", "erodible", and "absorbable" are used somewhat interchangeably in the literature in the field, with or without the prefix "bio". Herein, these terms will be used interchangeably to describe material broken down and gradually absorbed or eliminated by the body within five years, whether degradation is due mainly to hydrolysis or mediated by metabolic processes.

"Tensile modulus" is the ratio of stress to strain for a given material within its proportional limit.

"Tube" is defined as a long hollow cylinder with an outside diameter of 1 inch (2.54 cm) or less that is flexible.

II. Compositions

Methods have been developed to produce tubes from P4HB and copolymer thereof without radial deformation. The tubes are more flexible, with lower tensile modulus values, than PLLA tubes, and have higher elongation to break values than PLLA tubes. The tubes also degrade in vivo faster than PLLA tubes. The tubes may be used as implantable devices optionally after further processing.

A. Polymers

The methods described herein can typically be used to produce tubes from poly-4-hydroxybutyrate (Tepha's P4HB™ polymer) or a copolymer thereof. Copolymers include 4-hydroxybutyrate with 3-hydroxybutyrate, and 4-hydroxybutyrate with glycolic acid monomer or lactic acid monomer. P4HB and copolymers thereof can be obtained from Tepha, Inc. of Lexington, Mass. Preferred PHA polymers have a weight average molecular weight (Mw) of 50,000 to 1,200,000, preferably 100,000 to 1,000,000 and more preferably, 100,000 to 600,000 based on gel permeation chromatography (GPC) relative to polystyrene standards.

Polyhydroxyalkanaotes (PHAs) are produced by numerous microorganisms (see, for example, Steinbüchel A., et al. Diversity of Bacterial Polyhydroxyalkanoic Acids, *FEMS Microbial. Lett.* 128:219-228 (1995)). In nature these polyesters are produced as storage granules inside cells, and serve to regulate energy metabolism. They are also of commercial interest because of their thermoplastic properties, and relative ease of production.

P4HB and copolymers thereof can be produced using transgenic fermentation methods, see, for example, U.S. Pat. No. 6,548,569 to Williams et al., and are produced commercially, for example, by Tepha, Inc. (Lexington, Mass.). P4HB is not naturally occurring. P4HB is a strong, pliable thermoplastic polyester that, despite its biosynthetic route, has a relatively simple structure. Chemical synthesis of P4HB has been attempted, but it has been impossible to produce the polymer with a sufficiently high molecular weight that is necessary for most applications, including melt processing (see Hori, Y., et al., *Polymer* 36:4703-4705 (1995); Houk, K. N., et al., *J. Org. Chem.*, 2008, 73 (7), 2674-2678; and Moore, T., et al., *Biomaterials* 26:3771-3782 (2005)). In fact, it has been calculated to be thermodynamically impossible to chemically synthesize a high molecular weight homopolymer under normal conditions (Moore, T., et al., *Biomaterials* 26:3771-3782 (2005)). Chemical synthesis of P4HB instead yields short chain oily oligomers that lack the desirable thermoplastic properties of the high molecular weight P4HB polymers produced by biosynthetic methods.

It should be noted that the literature commonly refers to another polyhydroxyalkanoate, poly-3-hydroxybutyrate (P3HB), simply as polyhydroxybutyrate (PHB) (see Section 2 of Moore, T., et al., *Biomaterials* 26:3771-3782 (2005)). PHB has entirely different properties to P4HB. It is structurally and functionally different to P4HB. For example, PHB has a melting point of 180° C. versus a melting point of about 61° C. for P4HB. The polymers also have substantially different glass transition temperatures and mechanical properties. For example, PHB is a relatively hard brittle polymer with an extension to break of just a few percent, whereas P4HB is a strong extensible polymer with an extension to break of about 1000%. Substantially different conditions are required to process these two polymers, and the resulting products have substantially different properties.

U.S. Pat. Nos. 6,245,537, 6,623,748, 7,244,442, and 8,231,889 describe methods of making PHAs with little to no endotoxin, which are suitable for medical applications. U.S. Pat. Nos. 6,548,569, 6,838,493, 6,867,247, 7,268,205, 7,179,883, 7,268,205, 7,553,923, 7,618,448 and 7,641,825 and WO 2012/064526 describe use of PHAs to make medical devices. Copolymers of P4HB include 4-hydroxybutyrate copolymerized with 3-hydroxybutyrate or glycolic acid (U.S. Pat. No. 8,039,237 to Martin and Skraly, U.S. Pat. No. 6,316,262 to Huisman et al., and U.S. Pat. No. 6,323,010 to Skraly et al.). Methods to control molecular weight of PHA polymers have been disclosed by U.S. Pat. No. 5,811,272 to Snell et al.

PHAs with controlled degradation and degradation in vivo of less than one year are disclosed by U.S. Pat. Nos. 6,548,569, 6,610,764, 6,828,357, 6,867,248, and 6,878,758 to Williams et al. and WO 99/32536 to Martin et al. Applications of P4HB have been reviewed in Williams, S. F., et al., *Polyesters, III,* 4:91-127 (2002), Martin, D. et al. Medical Applications of Poly-4-hydroxybutyrate: A Strong Flexible Absorbable Biomaterial, *Biochem. Eng. J.* 16:97-105 (2003), and Williams, S. et al. Poly-4-hydroxybutyrate (P4HB): a new generation of resorbable medical devices for tissue repair and regeneration, *Biomed. Tech. (Berl)* ISSN (Online) 1862-278X, ISSN (Print) 0013-5585, DOI: 10.1515/bmt-2013-0009, 2013. Medical devices and applications of P4HB have also been disclosed by WO 00/56376 to Williams et al. Several patents including U.S. Pat. Nos. 6,555,123, 6,585,994, and 7,025,980 to Williams and Martin describe the use of PHAs in tissue repair and engineering. WO 2007/092417 to Rizk et al. discloses compositions of PLA toughened with P4HB suitable for medical applications.

WO 04/101002 to Martin, et al., U.S. Pat. No. 8,034,270 to Martin et al., U.S. Pat. No. 8,016,883 to Coleman et al., and U.S. Pat. No. 8,287,909 to Martin et al., WO 2011/119742 to Martin et al., WO 06/015276 to Rizk, and WO 2011/159784 to Cahil et al. disclose fibers, non-wovens, and textiles made by melt extrusion of P4HB.

B. Additives

Certain additives may be incorporated into P4HB, copolymers and blends thereof prior to converting these compositions into tubes. Preferably, these additives are incorporated during the compounding process to produce pellets that can be subsequently processed into tubes. In another embodiment, the additives may be incorporated using a solution-based process. In a preferred embodiment, the additives are biocompatible, and even more preferably the additives are both biocompatible and resorbable.

In one embodiment, the additives may be nucleating agents and/or plasticizers. These additives may be added in sufficient quantity to produce the desired result. In general, these additives may be added in amounts of up to 20% by weight. Nucleating agents may be incorporated to increase the rate of crystallization of the P4HB homopolymer, copolymer or blend. Such agents may be used to improve the mechanical properties of the tubes, and to reduce production times. Preferred nucleating agents include, but are not limited to, salts of organic acids such as calcium citrate, polymers or oligomers of PHA polymers and copolymers, talc, micronized mica, calcium carbonate, ammonium chloride, and aromatic amino acids such as tyrosine and phenylalanine.

Plasticizers that may be incorporated into the compositions include, but are not limited to, di-n-butyl maleate, methyl laureate, dibutyl fumarate, di(2-ethylhexyl) (dioctyl) maleate, paraffin, dodecanol, olive oil, soybean oil, polytetramethylene glycols, methyl oleate, n-propyl oleate, tetrahydrofurfuryl oleate, epoxidized linseed oil, 2-ethyl hexyl epoxytallate, glycerol triacetate, methyl linoleate, dibutyl fumarate, methyl acetyl ricinoleate, acetyl tri(n-butyl) citrate, acetyl triethyl citrate, tri(n-butyl) citrate, triethyl citrate, bis(2-hydroxyethyl) dimerate, butyl ricinoleate, glyceryl tri-(acetyl ricinoleate), methyl ricinoleate, n-butyl acetyl rincinoleate, propylene glycol ricinoleate, diethyl succinate, diisobutyl adipate, dimethyl azelate, di(n-hexyl) azelate, tri-butyl phosphate, and mixtures thereof. Particularly preferred plasticizers are citrate esters.

In another preferred embodiment, the additives are contrast agents, radiopaque markers, dyes, medical markers, and radioactive substances. These additives may also be incorporated into P4HB or copolymer thereof either before preparing tubes or after they are prepared.

C. Bioactive Agents

If desired, P4HB and copolymers thereof used to make the tubes may incorporate bioactive agents. These bioactive agents may be added during the formulation process, during pelletization or blending, or may be added later to the tubes.

In one embodiment, the bioactive agents and the P4HB or copolymer thereof may be dissolved in a solvent or solvent system in order to disperse the bioactive agent in P4HB or copolymer thereof, and the solvent may then be removed by evaporation. Preferred solvents include methylene chloride, chloroform, tetrahydrofuran, acetone, dimethylformamide, and 1,4-dioxane. The composition of P4HB or copolymer thereof with the bioactive agent may be extruded to form a tube.

Examples of bioactive agents that can be incorporated into the P4HB polymer or copolymer thereof, include, but are not limited to, small-molecule drugs, anti-inflammatory agents, immunomodulatory agents, molecules that promote cell migration, molecules that promote or retard cell division, molecules that promote or retard cell proliferation and differentiation, molecules that stimulate phenotypic modification of cells, molecules that promote or retard angiogenesis, molecules that promote or retard vascularization, molecules that promote or retard extracellular matrix disposition, signaling ligands, platelet rich plasma, anesthetics, antimicrobials, antibiotics, diagnostic agents, therapeutic agents, hormones, antibodies, growth factors, extracellular matrix or components thereof (fibronectin, laminin, vitronectin), integrins, antibiotics, antimicrobials, steroids, hydroxyapatite, silver particles, vitamins, non-steroidal anti-inflammatory drugs, chitosan and derivatives thereof, alginate and derivatives thereof, collagen, hyaluronic acid and derivatives thereof, allograft material, xenograft material, and ceramics. Representative materials include proteins, peptides, sugars, polysaccharides, nucleotides, oligonucleotides, lipids, lipoproteins, nucleic acid molecules such as antisense molecules, aptamers, siRNA, and combinations thereof.

D. Properties of the Tubes

In an embodiment, the inner diameter of the tube may be 0.5 mm to 9.5 mm, and the outer diameter of the tube may be 1 mm to 10 mm. The tubes produced by the methods herein described are more flexible than PLLA tubes, and have tensile modulus values of 60 to 700 MPa and have tensile strengths greater than 50 MPa, but less than 2 GPa. Preferably, the tube have tensile modulus values of 60 to 400 MPa, more preferably between 60 and 300 MPa and even more preferably, between 65 and 250 MPa. The tubes produced by the methods described herein may have very high elongation to break values. In an embodiment, the tubes have an elongation to break of 30% to 1,000%, more preferably 50% to 500% and even more preferably, between 100% and 300%. In another embodiment, the tensile strength of the tubes is 50 MPa to 2 GPa, and more preferably 50 MPa to 800 MPa.

III. Tubes of P4HB and Copolymers Thereof and Methods of Manufacturing

The methods disclosed herein are based on the discovery that tubes of P4HB and copolymers thereof can be produced using a continuous process, without radial deformation of the tubes despite the slow crystallization of the polymer or copolymers. The methods generally include the following steps: (i) drying pellets of the P4HB polymer or copolymer thereof so that the moisture content of the polymer or copolymer is less than 300 ppm water, (ii) introducing the pellets into a suitable extruder fitted with a metering pump and inline spiral type die, heating and melting the polymer or copolymer using a temperature profile of 60 to 270° C., (iii) radially expanding the tube at a temperature above the polymer or copolymer's melting temperature by injecting air or gas into the inner diameter of the extruded tube to define the inner diameter of the tube, (iv) allowing the extruded tube to exit the die into a quenching bath through an air gap, (v) drawing the extruded tube away from the extruder without distortion of the tubular geometry, (vi) allowing the tube a prolonged period to crystallize in the quench bath, and (vii) cutting the tube to the desired length.

A. Tube Extrusion

In order to successfully extrude tubes of P4HB and copolymers thereof without substantial loss of molecular weight, it is necessary to dry the resin prior to extrusion. In a preferred embodiment, the resin for extrusion should be dried so that it has a water content of less than 300 ppm. The polymer or copolymer may be dried, for example, using a rotary vane vacuum pump system. In addition to drying the resin prior to extrusion, it is desirable to protect the resin from water uptake when it is loaded into the extruder feed hopper. This may be achieved using, for example, a purge with dry nitrogen. In one embodiment, suitable tubes can be extruded by introducing the resin into an extruder barrel with heating zones set between 60° C. and 270° C. For example, an extruder with 8 heating zones may be used with temperatures set at 80° C., 140° C., 190° C., 205° C., 210° C., 220° C., 235° C. and 150° C. In a preferred embodiment, the extruder is fitted with a metering pump. Preferably, the die pressure is between 600 and 1,800 psi (4.14 MPa and 12.41 MPa), and the screw speed is preferably 1-5 rpm. In another preferred embodiment, the extruder is fitted with an inline spiral die preferably with an adjustable wall centering assembly. In a particularly preferred embodiment, the internal dimension of the tube is carefully controlled by injecting low pressure gas or air, preferably with a pressure of 2 to 4 inches of water (498-995 Pa of water), into the inner diameter of the extruded tube. In another particularly preferred embodiment, radial expansion of the tube is performed at a temperature above the melt temperature of the polymer or copolymer. Preferably, the tubes are expanded at a temperature between the melt temperature of the polymer or copolymer and 270° C. In the case of P4HB, the tubes are radially expanded at a temperature between 62° C. and 270° C., more preferably, at a temperature between 80° C. and 235° C.

In a particularly preferred method, the P4HB or copolymer thereof is extruded at a temperature between 80° C. and 235° C. with a die pressure of 600 to 1,800 psi (4.14 MPa and 12.41 MPa) and a screw speed of 1-5 rpm, and the tubes are formed using an air pressure of 2 to 4 inches of water (498-995 Pa of water) at an expansion temperature of 62° C. to 270° C.

B. Downstream Tube Collection

After exiting the die, the extruded tube is drawn away from the extruder, and in a preferred embodiment passes through an air gap before entering a quench bath. The air gap is preferably 2-1,000 mm, but more preferably 10-20 mm (measured between the die and the entry of the tube into the quenching medium). The extruded tube is preferably quenched in cold water. In a particularly preferred embodiment, the temperature of the cold water is from 1 to 25° C., preferably 4° C. to 15° C., more preferably 4° C. to 10° C., and even more preferably 4° C. to 6° C. In a preferred embodiment, the tube is cooled for 2 to 12 minutes, preferably 5 to 12 minutes, and even more preferably 6 to 12 minutes as it travels through the quench bath. In a particularly preferred method, the extruded tubes exiting the die pass through an air gap of 10-20 mm and are cooled at a temperature of 4-6° C. for 7-12 minutes. A suitable quench bath is preferably 2 to 24 feet (0.61 to 7.3 meters), and more preferably 20 to 24 feet (6 to 7.3 meters) in length when the tube is collected at 2-3 feet per minute (0.61 to 0.91 meters per minute). A preferred tube collection speed is 1-5 feet per minute (0.3 to 1.52 meters per minute). In a preferred embodiment, the quench bath is fitted with dams, diaphragms and weirs to keep the flow of the cooling water in the bath as constant as possible. This helps to prevent any alteration of the shape of the extruded tube as it enters the water and also as it is drawn through the bath. The extruded tube is pulled through the bath by a belt puller, and may be cut to the desired lengths using, for example, a series of fly knives. The wall thickness of the extruded tube may be monitored, for example, using ultrasonic sensors that create echoes from the outer and inner surfaces of the tube.

C. Methods of Coating the Tubes

In an embodiment, the tubes may be coated with other substances, such as additives, bioactive agents, and polymers, including dyes, medical markers, therapeutic agents, diagnostic agents, contrast agents, radiopaque markers, radioactive substances, antimicrobials, antibiotics, hyaluronic acid or derivatives thereof, collagen and hydroxyapatite. These substances may be applied to the tubes by any suitable means including, for example, solvent solution coating, spray coating, powder coating extrusion, latex coating, plasma treatment, cross-linking, covalent bonding and dip coating. If necessary, primer coatings may first be added to the tubes to improve adhesion of the substances. A topcoat, for example of a polymer, may also be applied to the tube to modify the release profile of a bioactive agent or to change the surface properties of the tube. In a preferred embodiment, bioactive agents are added to the tube using polymer solutions of a carrier for the bioactive agent. A preferred carrier is P4HB and copolymers thereof.

D. Methods of Preparing Implants from the Tubes

The extruded tubes described herein may be used without further modification as medical devices, such as catheter tubes, intravenous lines, dialysis tubing, sheaths for self-expanding stents, inflation lumens for balloons, suction lumens for atherectomy devices, and lumens for catheter-steering wires.

Alternatively, the tubes may be further processed to make medical devices. In one embodiment, the tubes may be used to prepare stents. The stent may be cut from the tube using a predefined stent design. The tube is preferably cut with a laser, and more preferably with a CO2 laser, Excimer laser or femtosecond laser.

In another embodiment, the tubes may be further machined to make medical devices or components of medical devices.

E. Sterilization

The tubes, or implants made from the tubes, may be sterilized by any suitable method including ethylene oxide, gamma-irradiation, and electron-beam irradiation. A particularly preferred method of sterilization is the use of cold ethylene oxide.

IV. Methods of Using the Tubes and Implants

In a preferred embodiment, the implants (including tubes and devices derived from the tubes) are delivered using minimally invasive techniques. For example, the implants may be delivered using a balloon catheter to insert the implant in the desired position. If desired, the implants may also incorporate one or more medical markers to aid the surgeon in the correct placement and orientation of the implant. One skilled in the art will appreciate that the tubes and devices derived from the tubes can also be delivered using more traditional surgery techniques, including open surgery.

The present invention will be further understood by reference to the following non-limiting example.

EXAMPLE 1

Melt Extrusion of P4HB to Produce a P4HB Tube

Poly-4-hydroxybutyrate (Tepha's P4HB polymer, Mw 575 kD) was ground, pelletized and dried to less than 300 ppm moisture under vacuum. A single lumen P4HB tube was melt extruded using an American Kuhne ¾" single screw extruder (24:1 L:D, 3:1 compression) equipped with a Zenith type metering pump (0.16 cc/rev) and an inline spiral type die with adjustable wall centering assembly. The 8 heating zones of the extruder were set at 80° C., 170° C., 230° C., 235° C., 230° C., 230° C., 200° C., and 150° C. (die). Low pressure air of 2-4 inch of water (498-995 Pa of water) was injected into the inner diameter of the extruded tube in order to define the inner diameter dimension and to assist in product cooling. The molten tube was cooled by passing it through two in-line water quench troughs of 20-24 feet (6.1-7.3 meters), leaving an air gap of 10-20 mm between the die and the first quench bath. The molten tube was guided into each quench trough through an iris and series of overflow dams. Water flowing through the iris provided support as well as cooling. Air wipers were fitted at the end of each trough to remove water droplets from the tube surface before further processing. Extrusion line speed was governed by a belt puller which drew the tube away from the extrusion die without distortion of the emerging tubular geometry. The collection speed was 2.45 fpm (0.75 meters per min). A cut-off device employing a series of fly knifes cut the tube to the desired length. Tube wall thickness was measured with a series of four ultrasonic sensors equally spaced and mounted to the frame of the first water trough. A second outer diameter measuring device using an X-Y optical laser was placed at the end of the second water trough to confirm the final product diameter.

The outside diameter of the P4HB tube was 0.102" (2.59 mm), and the inside diameter of the P4HB tube was 0.070" (1.78 mm). The tensile strength of the tube was 21.01 kgf, and the elongation to break was 293%.

EXAMPLE 2

P4HB Tube with Outside Diameter of 1.7 mm Produced by Melt Extrusion

A P4HB tube with an outside diameter of 1.7 mm, inside diameter of 1.35 mm, and wall thickness of 0.175 mm was produced using a procedure similar to that described in Example 1 using a P4HB polymer with a Mw of 575 kD. The extruder heating zones were set between 80° C. and 235° C., the air gap was set at 10-20 mm, and low pressure air of 2-4 inch of water (498-995 Pa of water) was injected into the inner diameter of the tube. A 20-24 feet (6.1-7.3 meter) trough was used for quenching the tube. The tube was tested and found to have the following properties: load 7.03 kgf (68.9 N), load at yield 4.1 kgf (40.2 N), elongation to break of 1,100%±200%, and tensile modulus of 231.3 MPa (23.6 kgf/mm$^2$).

EXAMPLE 3

P4HB Tube with Outside Diameter of 2.7 mm Produced by Melt Extrusion

A P4HB tube with an outside diameter of 2.7 mm, inside diameter of 2.2 mm and wall thickness of 0.25 mm was produced using the procedure of Example 2. The tube was tested and found to have the following properties: load 9.2 kgf (90.2 N), and a tensile modulus of 68 MPa.

Modifications and variations of the invention described herein will be obvious to those skilled in the art and are intended to come within the scope of the appended claims.

We claim:

1. A tube produced by a process comprising:
   extruding molten poly-4-hydroxybutyrate thermoplastic polymer or copolymer thereof through an annular passageway formed between a die and a mandrel to form an extruded tube,
   radially expanding the extruded tube at a temperature greater than the melt temperature of the polymer or copolymer to form a molten tube,
   cooling the molten tube in a cold water bath, and drawing the thus cooled tube away from the extruder thereby forming the tube,
   wherein the tube comprises an inner and outer diameter, and has a tensile strength greater than 50 MPa, but less than 2 GPa or an elongation to break of 30% to 1,100%.

2. The tube of claim 1 wherein the tube has an elongation to break of 30% to 1,100%.

3. The tube of claim 1 further comprising one or more of the following: medical marker, therapeutic agent, diagnostic agent, bioactive agent, antimicrobial, antibiotic, prophylactic agent, contrast agent, radiopaque marker, radioactive substance, hyaluronic acid or derivative thereof, collagen, and hydroxyapatite.

4. The tube of claim 1 wherein the outer diameter is 1 mm to 10 mm and the inner diameter is 0.5 mm to 9.5 mm.

5. The tube of claim 4 wherein the average outer and inner diameters of the tube varies less than ±0.003" inches (±0.08 mm).

6. A process for forming the tube of claim 1 comprising:
extruding molten poly-4-hydroxybutyrate thermoplastic polymer or copolymer thereof through an annular passageway formed between a die and a mandrel to form an extruded tube,
radially expanding the extruded tube at a temperature greater than the melt temperature of the polymer or copolymer to form a molten tube,
cooling the molten tube in a cold water bath, and
drawing the thus cooled tube away from the extruder thereby forming the tube of claim 1.

7. The process of claim 6 wherein (a) there is an air gap between the exit of the die and the surface of the water bath of 2-1000 mm; (b) the temperature of the cold water bath is from 1 to 25° C.; or (c) the cold water bath is longer than 2 feet (0.61 meters) and less than or equal to 24 feet (7.3 meters), and the tube is collected at a speed of 2 to 3 feet per minute (0.61 to 0.91 meters per minute).

8. The process of claim 7 wherein the temperature of the cold water bath is from 4 to 15° C.

9. The process of claim 8 wherein the molten tube is cooled in the water bath for 2 to 5 minutes.

10. The process of claim 8 wherein the molten tube is cooled in the water bath for 6 to 12 minutes.

11. The process of claim 7 wherein the cold water bath is 20 to 24 feet long (6.1 to 7.3 meters).

12. The process of claim 6 wherein: (a) the polymer or copolymer is dried to a moisture content of less than 300 ppm prior to extrusion; (b) the molten polymer or copolymer is heated to temperatures from 80° C. to 270° C.; or (c) pressurized air is introduced into the inner diameter of the extruded tube.

13. The process of claim 12 wherein the pressurized air has a pressure from 2 to 4 inches of water (498 to 995 Pa of water).

14. The process of claim 6 wherein there is an air gap between the exit of the die and the surface of the water bath of 10-20 mm.

15. The process of claim 6 wherein the temperature of the cold water bath is from 4 to 10° C.

16. The process of claim 6 wherein the extruded tube is radially expanded at 62° C. to 270° C.

17. The process of claim 6 wherein the polymer or copolymer further comprises one or more of the following: nucleant, plasticizer, dye, and ceramic.

18. The process of claim 6 wherein the tensile modulus of the tube is 60 to 700 MPa.

19. The process of claim 6 wherein the tube is an implantable device.

* * * * *